(12) United States Patent
Fisher et al.

(10) Patent No.: US 8,656,923 B2
(45) Date of Patent: *Feb. 25, 2014

(54) ORAL ORTHOSIS

(75) Inventors: Jeffrey Joe Fisher, Ada, MI (US); Scott Salmon, Tenafly, NJ (US); Josh Hartl, Bloomfield, NJ (US)

(73) Assignee: Ranir, LLC, Grand Rapids, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/609,835

(22) Filed: Sep. 11, 2012

(65) Prior Publication Data

US 2013/0000652 A1    Jan. 3, 2013

Related U.S. Application Data

(63) Continuation of application No. 12/652,387, filed on Jan. 5, 2010, now Pat. No. 8,322,344.

(51) Int. Cl.
*A61F 5/56* (2006.01)

(52) U.S. Cl.
USPC ............................ 128/848; 128/859; 128/861

(58) Field of Classification Search
USPC .......... 128/848, 859, 861–862; 433/6, 37, 44, 433/48; 602/902
See application file for complete search history.

(56) References Cited

U.S. PATENT DOCUMENTS

| | | | |
|---|---|---|---|
| 3,864,832 A | 2/1975 | Carlson | |
| 4,862,903 A | 9/1989 | Campbell | |
| 5,056,534 A | 10/1991 | Wright | |
| 5,092,346 A | 3/1992 | Hays et al. | |
| 5,117,816 A | 6/1992 | Shapiro et al. | |
| 5,277,202 A | 1/1994 | Hays | |
| 5,313,960 A | 5/1994 | Tomasi | |
| 5,462,066 A | 10/1995 | Snyder | |
| 5,601,093 A | 2/1997 | Sheehan | |
| 5,642,737 A | 7/1997 | Parks | |
| 5,692,523 A * | 12/1997 | Croll et al. | 128/859 |
| 5,715,840 A | 2/1998 | Hall | |
| 5,727,564 A | 3/1998 | Yannalfo | |
| 5,752,826 A | 5/1998 | Andreiko | |
| 5,915,385 A | 6/1999 | Hakimi | |
| 5,941,247 A | 8/1999 | Keane | |
| 6,129,084 A | 10/2000 | Bergersen | |
| 6,263,877 B1 | 7/2001 | Gall | |
| 6,792,942 B1 | 9/2004 | Ho et al. | |
| 6,877,513 B2 | 4/2005 | Scarberry et al. | |
| 6,964,571 B2 | 11/2005 | Andersen et al. | |
| 7,156,774 B2 | 1/2007 | Mohindra | |
| 7,178,529 B2 | 2/2007 | Kownacki | |

(Continued)

*Primary Examiner* — Tatyana Zalukaeva
*Assistant Examiner* — Camtu Nguyen
(74) *Attorney, Agent, or Firm* — Price Heneveld LLP

(57) ABSTRACT

An oral orthosis includes a holder in the shape of a mouthpiece, including a curved arcuate trough-like upper section which receives a formable material. The formable material does not occupy the entire trough but rather includes voids between the formable material and the inner surfaces of trough of the holder to allow expansion of the formable material into the voids during the molding process when tooth pressure is placed on the formable material. This design results in elimination of the excess formable material which otherwise would require removal by trimming. Additionally, the formable material is placed in the trough in a configuration which includes indexing indentations along the centerline of the material, such that, during the molding process, the mouthpiece containing the formable material is easily centered along the edges of the user's teeth to provide a precise fitting.

13 Claims, 2 Drawing Sheets

(56) References Cited

U.S. PATENT DOCUMENTS 7,328,698 B2 2/2008 Scarberry et al.
2006/0130850 A1 6/2006 Chen
2007/0028926 A1 2/2007 Kotani \* cited by examiner

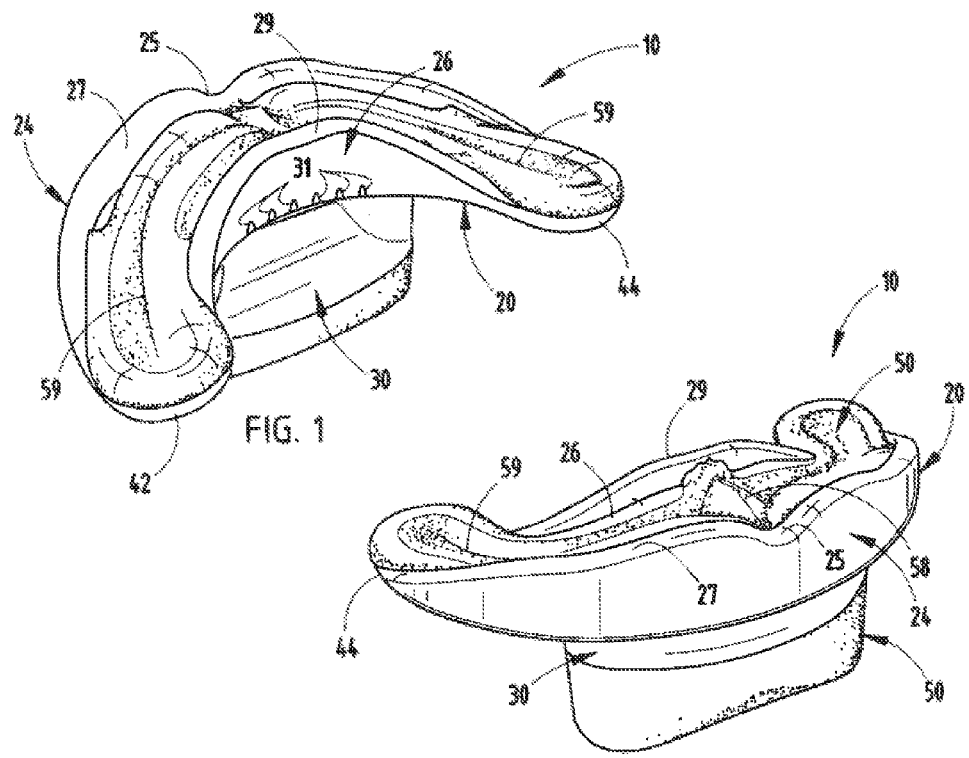
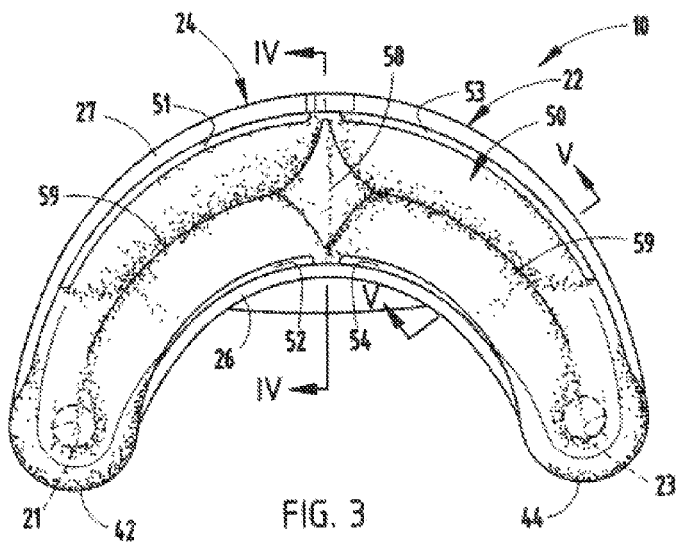

ORAL ORTHOSIS

CROSS-REFERENCE TO RELATED APPLICATIONS

This application is a continuation of U.S. patent application Ser. No. 12/652,387, filed on Jan. 5, 2010, entitled ORAL ORTHOSIS, by Jeffrey Joe Fisher et al., now U.S. Pat. No. 8,322,344, which issued Dec. 4, 2012, the entire disclosure of which is incorporated herein by reference.

BACKGROUND OF THE INVENTION

The present invention relates to an oral orthosis with improved molding characteristics.

Oral orthoses are typically shaped like mouthpieces which include a holder in the form of a curved tray made of a semi-rigid polymeric material, such as polycarbonate. The holder is filled with a moldable polymeric material for use by a dental professional or consumer in shaping the interior moldable content of the mouthpiece into a comfortable, tooth-conforming mouthpiece. Such orthoses are employed for in a variety of applications such as mouth guards for sporting events, bite guards to treat Bruxism at night, and snore prevention devices which are designed to urge the lower jaw slightly forwardly to provide clearance between the rear of the tongue and the uvula, which is the source of vibration causing objectionable snoring noise. The structure of the present invention can be employed in all such orthoses and in other similar applications; however, the invention is described in particular relationship to a snore prevention device.

Several such snore prevention devices are commercially available both for use by dentists and consumers directly in which the consumers position the unformed snore prevention device in boiling water and subsequently insert it in their mouths with their lower jaw projected forward slightly to allow the softened filler material to set and shape the mouthpiece, including the holder and moldable material, in a tooth-conforming configuration. Typically, both the upper and lower teeth are imprinted in the material which, when hardened, forms a finished snore prevention device which can be used on a nightly basis. With existing snore prevention devices, the filler material, however, when displaced by the teeth during the molding process, overfills the holder and results in excess material which is uncomfortable to the wearer's gums. The excess material must be trimmed and smoothed to provide the wearer with a comfortable finished product.

Thus, although snore prevention devices are effective in preventing or reducing snoring in individuals, the molding of the snore prevention devices by individuals and, particularly by the consumers themselves, frequently results in a less than desirable fit for comfort or, if a dental care professional is fitting such a device, it requires additional work, thereby increasing the cost to the consumer, There exists a need, therefore, for an improved snore prevention device which can be molded by the consumer, which is relatively inexpensive, easy to use, provides a comfortable fit, and is effective in preventing snoring.

SUMMARY OF THE INVENTION

The orthosis of the present invention satisfies this need by providing a holder in the shape of a mouthpiece, including a curved arcuate trough-like upper section which receives a formable material. The formable material does not occupy the entire trough but rather includes voids between the formable material and the inner surfaces of the trough of the holder to allow displacement of the formable material into the voids during the molding process when tooth pressure is placed on the formable material. This design results in elimination of the excess formable material which otherwise would require removal by trimming. Additionally, the formable material is placed in the trough in a configuration which includes indexing indentations along the centerline of the material, such that, during the molding process, the mouthpiece containing the formable material is easily centered along the edges of the user's teeth to provide a precise fitting.

In a preferred embodiment of the invention, the holder further includes air-escape apertures in at least one surface of the trough, such that, during the molding process, air can escape from the void as pressure is applied to the formable material, In another preferred embodiment of the invention, the trough filler material includes an indexing recess and tab, respectively, for centering the orthosis, such as a snore prevention device, with the front teeth. In such an application the holder further includes a lower pedestal which includes formable material to be impressed with the user's lower teeth and urge the user's lower jaw slightly forwardly during the molding process.

Thus, with the present invention, an improved orthosis is, provided that eliminates or greatly reduces any excess formable material resulting in a comfortable orthosis which can be easily employed by a consumer to provide a comfortable and effective device to reduce or eliminate snoring.

These and other features, objects and advantages of the present invention will become apparent upon reading the following description thereof together with reference to the accompanying drawings.

BRIEF DESCRIPTION OF THE DRAWINGS

FIG. 1 is a rear perspective view of a snore prevention device embodying the present invention;

FIG. 2 is a front perspective view of the snore prevention device shown in FIG. 1;

FIG. 3 is a top plan view of the snore prevention device shown in FIGS. 1 and 2;

DETAILED DESCRIPTION OF THE PREFERRED EMBODIMENT

Figure 4:
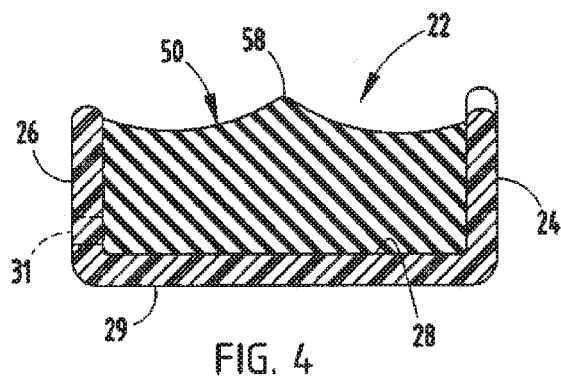
FIG. 4 is an enlarged cross-sectional view of the snore prevention device taken along section line IV-IV in FIG. 3.

Referring initially to FIGS. 1-3, there is shown a orthosis embodying the present invention. The invention can be employed for making a variety of different orthoses as noted above however, for purposes of illustration, an orthosis such as a snore prevention device 10 embodying the present invention is described as one preferred embodiment. The snore prevention device 10 comprises two basic elements including a semi-rigid outer member or holder 20 and a formable filler material 50 within the holder. The holder 20 is generally in the shape of a mouthpiece and includes an arcuate trough 22 (FIGS. 4-5) at an upper section thereof. The trough is defined by a front arcuate wall 24, a rear arcuate wall 26 spaced from said front wall, and a floor 28 (FIGS. 4 and 5) integrally joining the walls. Holder 20 also includes a downwardly projecting pedestal 30 integrally molded to the floor and coupled to the outer lower surface 29 (FIG. 6) of floor 28 by a pair of integral spaced-apart legs 32 and 34 defining an air transmission or breathing slot 40 between the lower surface 29 of trough floor 28 and the upper surface 35 of pedestal 30. Slot 40 extends through the snore prevention device 10 to provide a passageway for air between the lips of the user when the snore prevention device is in place.

Figure 5:
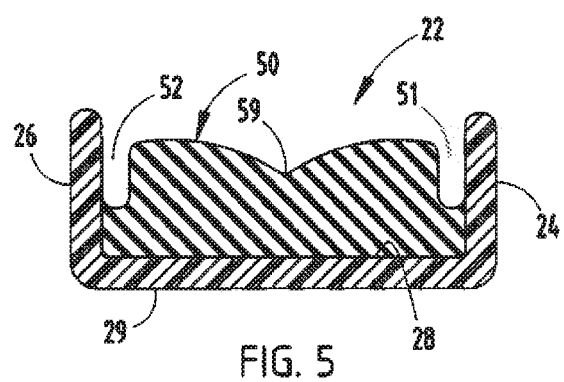
FIG. 5 is an enlarged cross-sectional view of the snore prevention device taken through section line V-V of FIG. 3.

The holder 20 is typically made of a resilient, semi-rigid polymeric material, such as polycarbonate or methylmethacrylate, although the thermoplastic resin preferred is polycarbonate made by the General Electric Company and sold under the trademark Lexan®. The three-dimensional shape of the holder 20 is molded in a conventional injection molding machine such that trough 22 of holder 20 is generally semicircular (as viewed from the top view of FIG. 3) and has a generally U-shaped cross section, as seen in FIGS. 4 and 5. The front wall 24 of the trough 22 is curvilinear and generally lip-shaped (i.e. generally higher toward the middle and shorter at the outer edges). Wall 24 has a concave indentation 25 at the center for assisting in centering the mouthpiece in alignment with the front teeth of a person's mouth during the molding process described below. The curvilinear top edge 27 of wall 24 curves downwardly toward the ends 42 and 44, which are substantially flat, and integrally join with the rear wall 26, which extends upwardly toward the center and is flattened at plateau 29, which is slightly lower than the notch 25 in the front wall 24. The holder includes air escape apertures and in one embodiment they are formed in the rear wall 26 which includes a plurality of apertures 31 (FIG. 1) which allow air to escape the trough 22 as teeth displace the formable material during the molding process described below.

Figure 6:
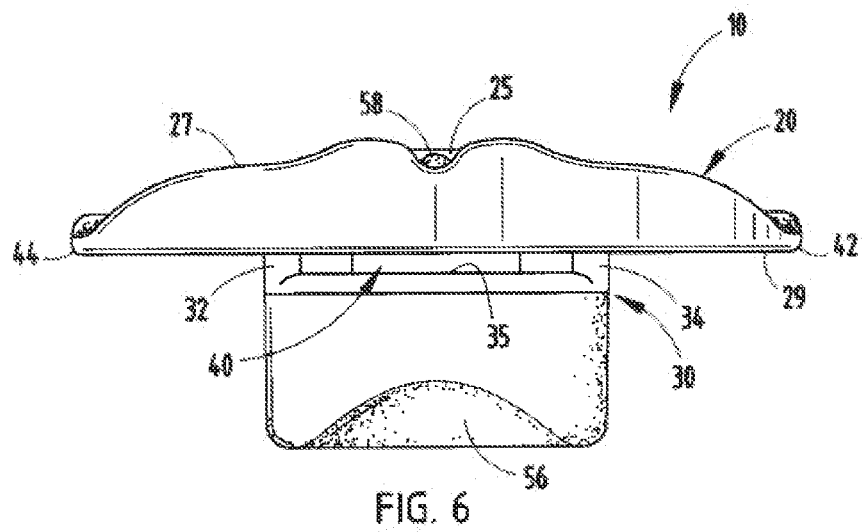
FIG. 6 is a front elevational view of the snore prevention device shown in FIGS. 1-3.
Figure 7:
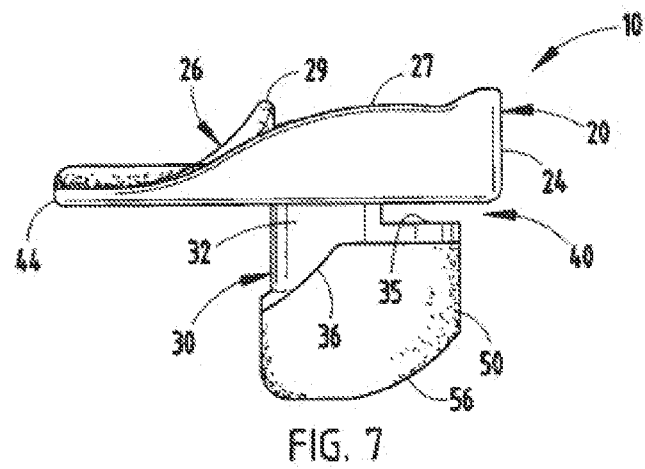
FIG. 7 is a right side elevational view of the snore prevention device shown in FIG. 6.

The formable or moldable material 50 which is positioned in the holder 20 for molding to the shape of the user's mouth and teeth preferably comprises an ethylene vinyl acetate copolymer resin. This material, or its equivalent, has a softening and molding temperature of between about 125° F.-175° F. and preferably about 150° F. Such material is sold by the E. I. DuPont de Nemours & Company under the trademark Elvax®. The material 50 is injection molded in a second molding step in which the holder 20 is positioned within a mold and the material 50, in the shape shown in FIGS. 1-7, is injection molded to partially fill the trough 22. The filler material is smaller than the trough 22, leaving voids 51 and 53 near the front wall 24 as best seen in FIG. 3, and voids 52 and 54 in the edges adjacent rear wall 26. This leaves, as also seen in FIG. 5, voids which allow the material 50 to flow into the trough 22 without overfilling and leaving excess material over the edges of the holder 20, Pedestal 30 likewise has formable material 50 injection molded in a curved pattern having a concavity 56, as best seen in FIGS. 6 and 7, and a ramp 36 to generally urge the lower jaw forwardly as the consumer forms the formable material 50 in his or her jaw between upper and lower teeth. Material 50, at the interface with pedestal 30, follows the inclined shape 36 of pedestal 30, as best seen in FIG. 7. The concavity 56 likewise represents a void into which the material 50 can be displaced during the fitting process, further reducing trimming.

The material 50 in the upper trough 22 includes a raised curvilinear indexing land 58 to provide a guide for centering the device in conjunction with the notch 25 located between the front teeth when placed in the user's mouth, The moldable insert material 50 also includes an arcuate alignment trough 59 on either side of the center land 58 which extends in an arcuate curve toward ends 42 and 44 for also assisting in centering the edges (i.e. biting surfaces) of the upper teeth within the holder 20 in alignment with the moldable filler material 50

In one embodiment of the invention, the arcuate length of the holder 20 along the outer wall 24 was about 3¼ inches and circumscribed and arc of approximately 180° and was substantially semicircular. The inner wall had an overall arc length of about 2¼ inches while the maximum depth of the trough 22 was approximately ¼ inch. Voids 51-54 have a gap width of approximately from about 0.030 to about 0.070 inches and in one embodiment were 0.040 inches. The voids have a depth of from about 0.030 inches to about 0.190 inches and in one embodiment had a depth of approximately 0.190 inches at the deepest section near the crown in wall 24 adjacent notch 25. The arc length for the front pair of voids 51, 53 are about 0.70 inches each and the rear pair 52, 54 are about 0.40 inches each. It is important that the sum of the volume of the voids are close to the average sum of the volume of the average teeth that will form the impressions. That can be accomplished by varying the proportions and/or number of voids. The limiting factor to any configuration is that the teeth should be adequately surrounded after forming to maintain the proper position of the orthosis.

Breathing slot 40 is sized to provide sufficient air for comfortable breathing and is tapered from front to back. In one embodiment it had an opening at the front of about 0.75 inches when viewed from FIG. 6 and is tapered rearwardly to an opening of approximately 0.06 inches at the rear of the slot. Its height (in one embodiment) was approximately 0.1 inch. These dimensions of the mouthpiece can be varied, although the dimensions given are for a snore prevention device which will comfortably fit most averaged sized mouths. The molded insert material 50 naturally adheres to holder 22; however, the floor 28 of holder 22 includes two circular apertures 21 and 23, as seen in FIG. 3, for receiving material 50 for locking it securely in place.

In use, the orthosis shown in the figures is held by a suitable holder (not shown) a vessel of boiling water for a period of time such that the formable material becomes softened. Since material 50 has a significantly lower softening temperature than that of the polycarbonate holder 20, immersion of the device in a heated fluid, such as boiling water, prior to fitting softens the material 50 to accept the user's tooth pattern. The fitting is accomplished by removing the snore prevention device 20 from the boiling water, allowing it to cool for a short period of time, and inserting the device into the user's mouth with the notch 25, indexing land 58, and alignment trough 59 guiding the positioning of the device into one's mouth. The tapered concavely curved edge 56 engages the inside of the lower teeth and tends to move the jaw slightly forwardly during the molding process. The user need only grip the snore prevention device between his/her teeth for 30 seconds or so to allow the thermoplastic filler 50 to set in a comfortable, upper and lower teeth engaging configuration, whereupon the device can be removed. It then contains a permanent imprint of the user's upper and lower teeth in which the lower teeth engage edge 56 of the pedestal to urge the lower jaw slightly forwardly in an amount of typically from about 2 mm to about 6 mm, sufficient to provide clearance between the back of the tongue and uvula to prevent or greatly reduce snoring during sleep.

The durable material is employed for the snore prevention device 10 to hold its shape and be useful for a significant amount of time and can be periodically sanitized as desired by the user and stored when not in use. Although the dimensions given are for medium sized snore prevention devices, it should be understood that the dimensions can be proportionally varied to make larger or smaller snore prevention devices as desired. The provision of the self-alignment guides, as well as the voids and air escape apertures or vents, provides an orthosis which, upon impressing the tooth pattern, does not result in an excess amount of material which must be trimmed for comfort and allows immediate use without such a step. The formable material 50 and/or the holder 20 can be colored to color code the snore prevention device for an individual user.

It will become apparent to those skilled in the art that various modifications to the preferred embodiment of the invention as described herein can be made without departing from the spirit or scope of the invention as defined by the appended claims.

The invention claimed is:

1. A custom-fitted oral care orthosis comprising;
 a semi-rigid non-formable holder defining a curved tray-like mouthpiece having a front arcuate wall and a rear arcuate wall, each with curved areas; and
 a formable material overlaying said holder for allowing said formable material to be custom fitted to the teeth of a user by impressing the teeth into the formable material, wherein said formable material is spaced from at least one of said front and rear walls of said holder in the curved area of said at least one of said front and rear walls to provide least an arcuate void located near a forward facing section of said front arcuate wall between said formable material and said front arcuate wall, such that, during the impressing process, the formable material displaced by the teeth extends into said void in a direction toward said front arcuate wall.

2. The orthosis as defined in claim 1 wherein said void is of sufficient width to allow said formable material to conform to a person's teeth without overflowing said holder.

3. The orthosis as defined in claim 1 wherein said holder includes an arcuate trough having a floor and spaced-apart front and rear walls with inner surfaces, said floor including an outer surface.

4. The orthosis as defined in claim 3 wherein said arcuate trough includes at least one aperture therein to allow air to escape when said formable material is compressed during molding by the user's teeth.

5. The orthosis as defined in claim 4 wherein said rear wall of said trough includes a plurality of apertures to allow air to escape when said formable material is compressed during molding by the user's teeth.

6. A custom-fitted oral care orthosis comprising;
 a semi-rigid non-formable holder defining a curved tray-like mouthpiece having front and rear curved walls with curved areas; and
 a formable material overlaying said holder for allowing said formable material to be custom fitted to the teeth of a user by impressing the teeth into the formable material, wherein said formable material is spaced from at least one of said front and rear walls of said holder in the curved area of said at least one of said front and rear walls to provide a void between said formable material and said one of said walls, such that, during the impressing process, the formable material displaced by the teeth extends into said void in a direction toward said at least one of said front and rear walls, wherein said void is of sufficient width to allow said formable material to conform to a person's teeth without overflowing said holder, and wherein said void is about 1/16 inches wide.

7. The orthosis as defined in claim 6 wherein voids are located between both said front wall and said rear wall of said holder and said formable material.

8. A snore prevention oral orthosis for molding to conform to a user's mouth comprising:
 a semi-rigid holder including an arcuate trough having a floor and a spaced-apart front arcuate wall and a rear arcuate wall with curved areas and inner surfaces; and
 a formable material positioned in said arcuate trough in spaced relationship to said inner surfaces of said front arcuate wall and rear arcuate wall in the curved area of said front and rear arcuate walls leaving arcuate voids between said formable material and said front arcuate wall and said rear arcuate wall, such that, when said formable material is deformed by impressing teeth therein, said formable material displaced by the teeth extends into said arcuate voids in a direction toward said front arcuate wall and said rear arcuate wall.

9. The orthosis as defined in claim 8 wherein said arcuate voids are of sufficient width to allow said formable material to conform to a person's teeth without overflowing said holder.

10. A snore prevention oral orthosis for molding to conform to a user's mouth comprising:
 a semi-rigid holder including an arcuate trough having a floor and spaced-apart front and rear curved walls with curved areas and inner surfaces; and
 a formable material positioned in said arcuate trough in spaced relationship to at least one of said inner surfaces of said front and rear walls in the curved area of said at least one of said walls leaving at least one void between said formable material and said holder such that when said formable material is deformed by impressing teeth therein said formable material displaced by the teeth extends into said void in a direction toward said at least one of said front and rear walls, wherein said void is of sufficient width to allow said formable material to conform to a person's teeth without overflowing said holder, and wherein said void is about 1/16 inches wide.

11. The orthosis as defined in claim 10 wherein voids are located between both said front wall and said rear wall of said holder and said formable material.

12. The orthosis as defined in claim 11 wherein said arcuate trough includes at least one aperture therein to allow air to escape when said formable material is compressed during molding by the user's teeth.

13. The orthosis as defined in claim 12 wherein said rear wall of said trough includes a plurality of apertures to allow air to escape when said formable material is compressed during molding by the user's teeth.

* * * * *

UNITED STATES PATENT AND TRADEMARK OFFICE
CERTIFICATE OF CORRECTION

| | | |
|---|---|---|
| PATENT NO. | : 8,656,923 B2 | Page 1 of 1 |
| APPLICATION NO. | : 13/609835 | |
| DATED | : February 25, 2014 | |
| INVENTOR(S) | : Fisher et al. | |

It is certified that error appears in the above-identified patent and that said Letters Patent is hereby corrected as shown below:

In the Claims

Column 5, claim 1, line 26,
    After "provide" insert --at--.

Signed and Sealed this
Fourteenth Day of October, 2014

Michelle K. Lee
*Deputy Director of the United States Patent and Trademark Office*